US 6,314,315 B1

(12) United States Patent
Hung et al.

(10) Patent No.: US 6,314,315 B1
(45) Date of Patent: Nov. 6, 2001

(54) DUCTAL ORIFICE IDENTIFICATION BY CHARACTERISTIC ELECTRICAL SIGNAL

(75) Inventors: David Hung, Belmont; Roger A Stern, Cupertino; Morton Grosser, Menlo Park, all of CA (US)

(73) Assignee: Pro Duct Health, Inc., Menlo Park, CA (US)

( * ) Notice: Subject to any disclaimer, the term of this patent is extended or adjusted under 35 U.S.C. 154(b) by 0 days.

(21) Appl. No.: 09/482,145

(22) Filed: Jan. 12, 2000

Related U.S. Application Data

(60) Provisional application No. 60/115,787, filed on Jan. 13, 1999.

(51) Int. Cl.⁷ .................................................. A61B 5/05
(52) U.S. Cl. ........................... 600/547; 600/554; 128/898
(58) Field of Search ..................... 600/547, 372, 600/382, 554; 128/898; 607/1, 901

(56) References Cited

U.S. PATENT DOCUMENTS

| | | | |
|---|---|---|---|
| 4,291,708 | 9/1981 | Frei et al. | 600/547 |
| 4,458,694 | 7/1984 | Sollish et al. | 600/547 |
| 4,493,039 | 1/1985 | Gregory | 324/228 |
| 5,025,790 | 6/1991 | Dias | 600/459 |
| 5,143,079 | 9/1992 | Frei et al. | 600/547 |
| 5,217,014 | 6/1993 | Hahn et al. | 600/397 |
| 5,255,677 | * 10/1993 | Schaefer et al. | 600/384 |
| 5,271,413 | 12/1993 | Dalamagas et al. | 600/547 |
| 5,320,101 | 6/1994 | Faupel et al. | 600/407 |
| 5,501,230 | 3/1996 | Laribiere | 600/508 |
| 5,560,357 | 10/1996 | Faupel et al. | 600/345 |
| 5,630,426 | 5/1997 | Eggers et al. | 600/547 |
| 5,660,177 | 8/1997 | Faupel et al. | 600/382 |
| 5,678,547 | 10/1997 | Faupel et al. | 600/409 |
| 5,697,369 | 12/1997 | Long, Jr. et al. | 600/407 |
| 5,732,704 | * 3/1998 | Thurston et al. | 600/431 |
| 5,732,710 | * 3/1998 | Rabinovich et al. | 600/547 |
| 5,810,742 | 9/1998 | Pearlman | 600/547 |
| 5,823,957 | 10/1998 | Faupel et al. | 600/397 |
| 5,833,634 | * 11/1998 | Laird et al. | 600/587 |
| 5,928,150 | * 7/1999 | Call | 600/436 |
| 6,168,779 | * 1/2001 | Barsky et al. | 424/9.2 |

FOREIGN PATENT DOCUMENTS

| | | |
|---|---|---|
| WO 9612439 | 5/1996 | (WO) . |
| WO 9705898 | 2/1997 | (WO) . |

\* cited by examiner

Primary Examiner—Eric F. Winakur
Assistant Examiner—Charles Marmor, II
(74) Attorney, Agent, or Firm—Banner & Witcoff, Ltd.

(57) ABSTRACT

The invention provides methods and kits relating to identification of ductal orifices on a mammalian breast nipple. The methods employ technology to measure characteristic electrical signals on a nipple surface to locate and image or map the ductal orifices on the nipple surface. Kits are also provided comprising materials for identifying a duct by characteristic electrical signal, and for additionally analyzing the signals, and accessing or marking the ducts once they have been identified by the characteristic electrical signal values.

25 Claims, 5 Drawing Sheets

DUCTAL ORIFICE IDENTIFICATION BY CHARACTERISTIC ELECTRICAL SIGNAL

CROSS-REFERENCE TO RELATED APPLICATIONS

This application claims the benefit of provisional application No. 60/115,787, filed on Jan. 13, 1999, under 37 CFR §1.78, the full disclosure of which is incorporated herein by reference.

BACKGROUND OF THE INVENTION

1. Field of the Invention

The field of this invention is use of a characteristic electrical signal to identify the location of milk duct orifices on mammalian breast nipples for purposes including accessing one or more of the milk ducts.

Analysis of ductal secretions from human breasts has been used to diagnose biological conditions of the breast ducts (1–4; see list of references hereinafter). The human nipple has from 6 to 12 ducts, and most of these studies pooled secretions or nipple aspirate fluid (NAF) for the analysis. Thus, the secretions of an individual duct are not identified in these studies. More recently, breast duct access has been incorporated into ductal fluid analyses and study protocols (5–7). Various methods have been employed in order to identify the breast ducts for purposes including duct fluid analysis (8–15). Additionally, breast ducts have been accessed by ductscope (15, 16). Ductal cannulation is proposed for delivery of agents (WO 97/05898 and (20)). Ductography, or mammary duct contrast examination, involves cannulation and injection of a ductal orifice (17–19), a process that is generally painless and devoid of complications (20).

Ductal access is also required for performing lavage procedures on a milk duct to deliver an agent and/or to retrieve cells from the duct for analysis as described in co-pending and co-owned or licensed applications including Ser. No. 09/067,661; 09/301,058; PCT US99/09141; 60/122,076; 09/313,463; 60/143,359; and application Ser. Nos. 09/473,510, filed Dec. 28, 1999, all incorporated by reference in their entirety. The challenge for the procedure can be finding a duct, or multiple ducts, for access.

It would therefore be desirable to provide improved methods, devices, and kits for accessing breast ducts. More particularly, it would be desirable to provide for the improved detection and identification of individual ductal orifices to facilitate subsequent ductal access for diagnostic and/or therapeutic purposes. Such methods, devices, and kits should be convenient and relatively simple to use, should present the patient with minimal or no discomfort, and should be highly reliable, i.e., should be able to detect all individual ductal orifices in a nipple in all or most cases. At least some of these objectives will be met by the invention described hereinafter.

2. Relevant Literature

WO 96/12439 assigned to TransScan Research & Development Corporation describes electrical impedance imaging devices having multi-element probes for providing electrical connection to tissue surfaces, particularly for detection of cancer in a live tissue, including breast tissue. U.S. Pat. No. 5,810,742 assigned also to TransScan describes an apparatus for making a tissue characterization in order to identify anomalous tissue. Faupel and Hsu, (1996) *Electropotentials in the clinical assessment of breast neoplasia*, Dixon eds. pp.37–44 describe measuring and analysis of skin potentials for cancer diagnosis. U.S. Pat. No. 5,678,547 to Biofield Corp. describes use of an electromagnetic field present between a reference and plurality of test points on a living organism to measure a gradient of electrical activity that occurs as a function of biological activity in order to monitor efficacy of a treatment for the disease, injury or bodily function. U.S. Pat. No. 4,291,708 and U.S. Pat. No. 4,458,694 to Yeda Research & Development Co. describe apparatus and methods for detecting tumors in living human breast tissue including instrumentalities for determining the dielectric constants of a plurality of localized regions of living human breast tissue.

SUMMARY OF THE INVENTION

The present invention provides methods, apparatus, and kits for identifying individual ductal orifices on a nipple surface of a mammalian breast, typically a human female breast. The methods comprise engaging at least one reference electrode against a body surface of the mammal (on the breast or elsewhere) and at least one test electrode against a test location on a surface of the nipple. An electrical current and/or potential is applied between the reference electrode and the test electrode, and a characteristic electric signal produced in response to the applied electrical current and/or potential is measured. The measured value is compared to a base or reference value in order to determine whether the test location is at or near a ductal orifice. Usually, the base electrical value will be a predetermined value, e.g., an average or typical value expected for nipple surface locations which do not comprise the ductal orifice. Alternatively, the base electrical value could be determined for each individual patient, e.g., as an average value determined over a large number of locations on the individual nipple surface where particular measured values at particular locations which differ from the average value determined for that patient will then be likely locations for ductal orifices. The reference electrode will usually be located on the body of the mammal at a location remote from the nipple surface, for example, at the base of the nipple, at the base of the breast, or elsewhere on an abdominal or chest surface of the mammal. Alternatively, in some instances, it will be possible (although generally not preferred) to measure the electrical characteristics between adjacent, laterally spaced-apart locations on the nipple surface in a bipolar manner. Such an approach will determine the surface electrical characteristics of the nipple. Generally, however, it will be preferred to measure electrical characteristic determined from the nipple surface through the "body" of the nipple to an external surface location remote from the nipple.

The test electrode(s) can be applied to the nipple surface in a variety of ways and in a variety of configurations. Most simply, the test electrode can comprise a single electrode element which may be contacted sequentially at multiple points on the nipple surface, either manually or using an automated positioning system. Electrical characteristic values can then be collected or displayed in a variety of ways. Most simply, electrical impedance or other values can be displayed to the person running the test. The person can then observe the value and note changes in electrical characteristics which denote the likelihood of the presence of a ductal orifice. Such manual or semi-automated approaches will be particularly valuable in conjunction with visual confirmation of the presence of an orifice. For example, detection of a change in the electrical characteristics may alert the person running the test to visually scan that area of the nipple more carefully for the presence of the orifice. Alternatively, the individual may simply collect data which is then transmitted to a data collection and analysis system, typically a digital analyzer such as a personal computer.

Alternatively, the test electrode may comprise an array of individual electrodes or electrode nodes which may be simultaneously engaged against a nipple surface or the entire nipple surface in order to generate multiple values of electrical characteristics without the need to reposition the electrode structure being used. In a first instance, the electrode structure could be an electrode array in the form of a patch, membrane, or other flexible support structure which can be applied against the breast, typically using an electrically conductive gel. The array can have a very large number of electrode points or nodes permitting the generation of a map of electrical values over the entire nipple surface. Usually, the map will be generated by sequentially interrogating each of the electrode nodes or elements in order to determine the characteristic electrical value at the position of that node. The data can be collected over a very short time and the map generated using appropriate data collection and digital analysis equipment. The map can then be presented visually, e.g., on a viewing screen, or numerically. Alternatively, the electrode array could be configured (or a separate system provided) to mark locations on the nipple surface which are likely to comprise a ductal orifice.

Alternatively, the electrode arrays can be configured as part of a probe which will usually have a smaller number of the individual electrodes or electrode nodes at its distal end. The electrode probe can then be applied over discrete areas of the nipple surface, usually requiring a number of successive placements of the electrode array in order to cover the entire nipple surface.

The electrical current and/or potential applied between the reference electrode(s) and test electrode(s) may comprise direct current, alternating current, high frequency alternating current, or any other type of electrical signal which can be applied to the patient in a safe and generally painless manner and produce a responsive signal that can be detected and which will vary depending on the proximity of a ductal orifice. In the specific embodiments, the electrical signal is typically a low frequency signal, e.g., having a frequency in the range from 1 kHz to 10 kHz. The responsive signal measured is electrical impedance.

The electrical impedance or other characteristic signal is usually measured using the reference electrode(s) and test electrode(s). For example, in the case of electrical impedance, measurements can be made based on the known voltage and current being applied between the test electrode and reference electrode. Other conventional systems for applying electrical energy and measuring characteristic responses are well-known in the patent and medical literature.

The present invention still further comprises kits including at least one reference electrode and one test electrode capable of being engaged against the nipple and other body surfaces as described above. Usually, the test kits will further comprise instructions for use setting forth any of the methods described above. Additionally, the kits may include elements for accessing a ductal orifice after it has been identified, elements for marking an ductal orifice after it has been identified, conductive gels for use in combination with electrode arrays, and the like. The kits may further comprise packaging for holding the kit components, usually in a sterile manner, instructions for use may be printed on separate package inserts, and/or be printed in whole or in part on the packaging itself.

DESCRIPTION OF THE SPECIFIC EMBODIMENTS

Figure 1:
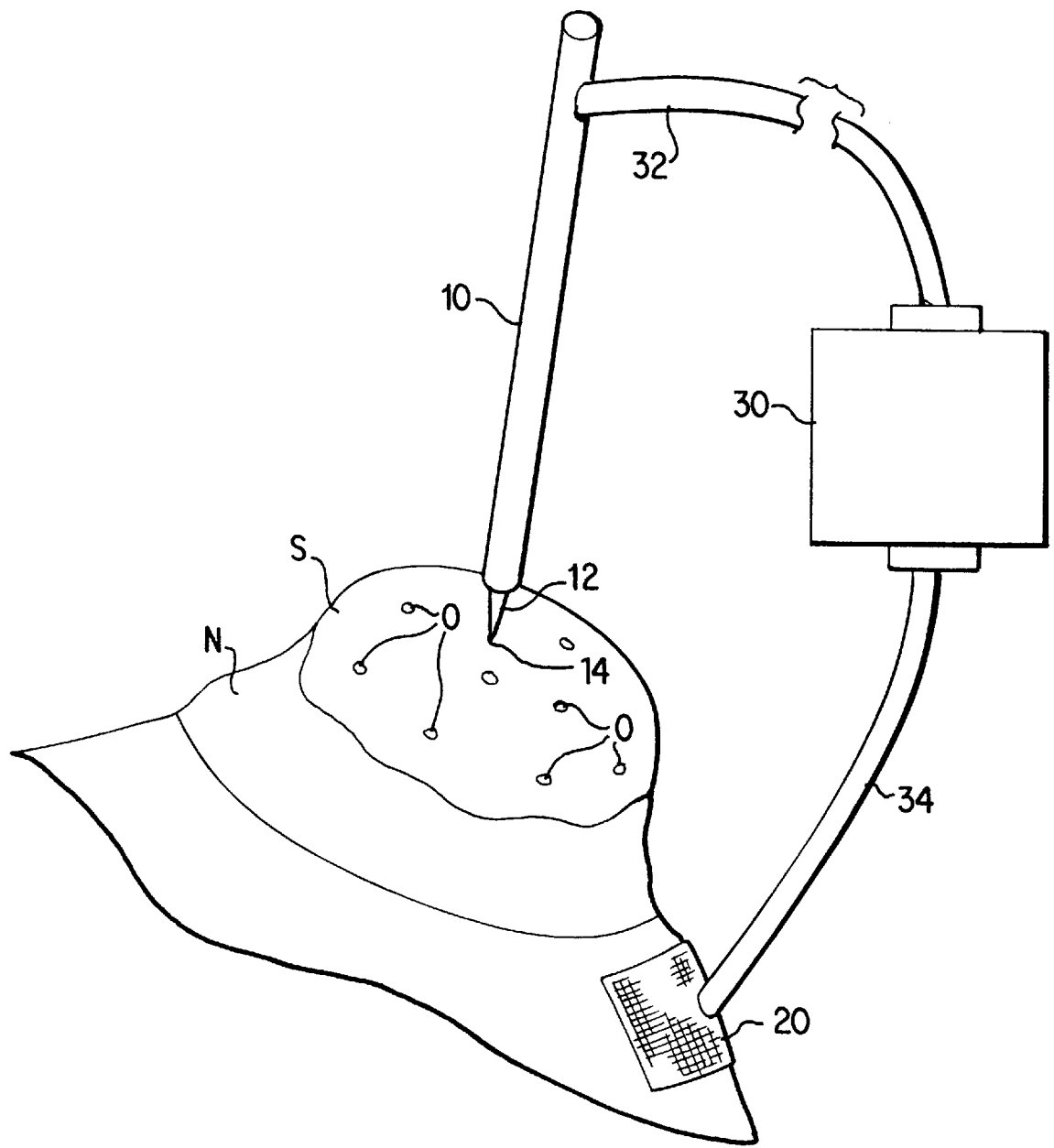
FIG. 1 shows a single electrode configuration.

The following preferred embodiments and examples are offered by way of illustration and not by way of limitation.

The method is practiced to identify a milk duct orifice or orifices on a mammalian nipple surface. The mammal can be any mammal e.g., a mammal having breasts with nipples, thus including e.g., humans, primates, pigs, dogs, cows, horses, rabbits, rats, cats and mice. Generally, the purpose of locating the ductal orifice is so that the duct can be accessed through the orifice, e.g., for delivering an agent to the duct and/or retrieving cellular and other materials from the duct. The agent can be e.g., saline for washing the duct and retrieving cells from the duct, or e.g., a therapeutic agent.

The method comprises new uses for electrical technology for the purpose of locating, imaging and/or mapping the locations of ductal orifices. An electrical circuit is created using a reference electrode and a test electrode and a machine capable of generating an electrical current and/or potential between the two electrodes, or between more than one electrode and a reference electrode. The reference electrode is placed on the body someplace other than the location where the test electrode is placed. The test electrode is generally placed on the nipple surface in order to attempt to identify the location of a breast duct orifice. A characteristic electrical signal is generated upon placement of the test electrode on the nipple surface. The characteristic electrical signal can be e.g., values of impedance, resistance, capacitance, inductance or reactance, or any electrical signal capable of conveying information to differentiate a location of the test electrode at a ductal orifice or not at a ductal orifice on a nipple surface.

The characteristic electrical signal can be compared to a reference value in order to identify the likelihood that the test location is a ductal orifice or not. The reference value can be predetermined, and thus the reference value can be e.g., the results of a cumulative survey of values of the particular electrical signal for ductal orifices or non-ductal orifices in order to help determine when a test electrode is most likely at a ductal orifice. Thus, e.g., a reference value might indicate a value below which a test electrode is most likely at a ductal orifice and above which a test electrode is most likely not at a ductal orifice. A reference electrode is located at a different location on the body than the test electrode. For example, the reference electrode can be on the body of the mammal being studied at a location including e.g., the base of the breast being studied, the base of the nipple being studied, the surface of the nipple being studied (albeit at a different location on the nipple surface than the test electrode), the areola of the nipple being studied, or the trunk of the mammal. The reference electrode can be affixed to its location on the mammalian body in any way that is safe to the patient and provides continuous contact with the skin surface, e.g., an adhesive pad comprising the electrode that contacts the skin surface. The reference electrode can have a lead connected to it that provides connection to the machine source that both generates a potential and measures the characteristic electrical signal. The reference (or return or emitting) electrode can be positioned as described in U.S. Pat. No. 5,143,079, WO 96/12439, or U.S. Pat. No. 5,810, 742 especially where descriptions are refined for studies of the human breast.

A test electrode is placed on the nipple surface. A single test electrode can be used, and in that case the test electrode is placed sequentially at different locations on the nipple surface and a value of characteristic electrical signal is taken at each different location relative to a reference value which can be a predetermined value and using also a reference electrode placed at a reference point on the body of the mammal. The test electrode can be set up to "scan" the surface of the nipple and thus to contact in fast succession multiple locations on the nipple surface. The scanning process provides multiple electrical signals so that the test electrode can test a large portion of the nipple surface rapidly. An identification signal such as a visual or auditory signal can be established when the test electrode had identified a location on the nipple surface likely to be a ductal orifice.

Alternatively, the test electrode can comprise multiple electrodes placed at he surface of the nipple. In the case of multiple test electrodes, a potential is applied between the reference and test electrodes, where each test electrode participates in a circuit with the reference electrode in succession.

In a simple format, the invention contemplates a method of identifying a ductal orifice by applying an electrical potential and/or current to the mammalian breast using a reference electrode placed at a reference point on the body of the mammal, and then applying a test electrode to a first and then a second and/or subsequent locations on the nipple surface and measuring a first and then a second value of characteristic electrical signal. If the test electrode is a single electrode then the test electrode is placed at the first location and then physically picked-up and moved to a second location on the nipple surface for the second location. If there are multiple test electrodes sitting on the nipple surface, a switcher can switch the potential and/or current successively from a first electrode to a second electrode thus generating a first and second value of a characteristic electrical signal from a first and second location on the nipple surface. Ultimately, a comparison of values between the first and second locations can be generated such that a ductal orifice is identified upon detection of a differential value of characteristic electrical signal. Alternatively, and preferably, any given electrical signal at a given test location is compared to a predetermined reference value for making an absolute determination of likelihood that the electrode has identified a ductal orifice.

FIG. 1 illustrates a first embodiment of the apparatus and method of the present invention. An electrode structure 10 comprising a single test electrode 12 is adapted for manual manipulation, e.g., it may be in the form of simple "pencil" structure having a shaft that can be manually grasped The electrode 12 will typically have a tapered or pointed tip 14 which is engaged directly against the surface S of the nipple N. A separate surface or counterelectrode 20 is provided and adapted for attachment to a body surface remote from the nipple. As shown in FIG. 1, the reference electrode 20 is mounted on the breast just below the nipple N. Reference electrode 20 could, of course, be mounted at any of the other body locations described elsewhere herein. The test electrode 12 is connected to an analyzer 30 via cable 32. Similarly, the reference electrode 20 is connected to the analyzer 30 via a cable 34. The analyzer 30 may have a wide variety of configurations as described elsewhere herein. Typically, the analyzer 30 will include at least a source of electrical current and circuitry for analyzing that current. The analysis circuitry may be included wholly within a single analyzer 30, or the analyzer 30 may be adapted to interface with other analyzer circuitry, such as in the form of a personal computer or other digital, programmable analyzer. Usually, at least the test electrode 12 and reference electrode 20 will be disposable and thus detachable from their respective cables 32 and 34. Alternatively, the entire cable structures may also be disposable and thus detachable from the analyzer 30.

The test electrode 12 of FIG. 1 will usually be used manually, where an operator successively engages the tip 14 of the electrode 12 against different test locations on the surface S of the nipple N. At each location, an impedance or other electrical characteristic value is measured. The measured value may be displayed, recorded or both, and the acquired data is eventually relied on to determine those locations on the nipple surface which are most likely to comprise an individual ductal orifice O.

Figure 2:
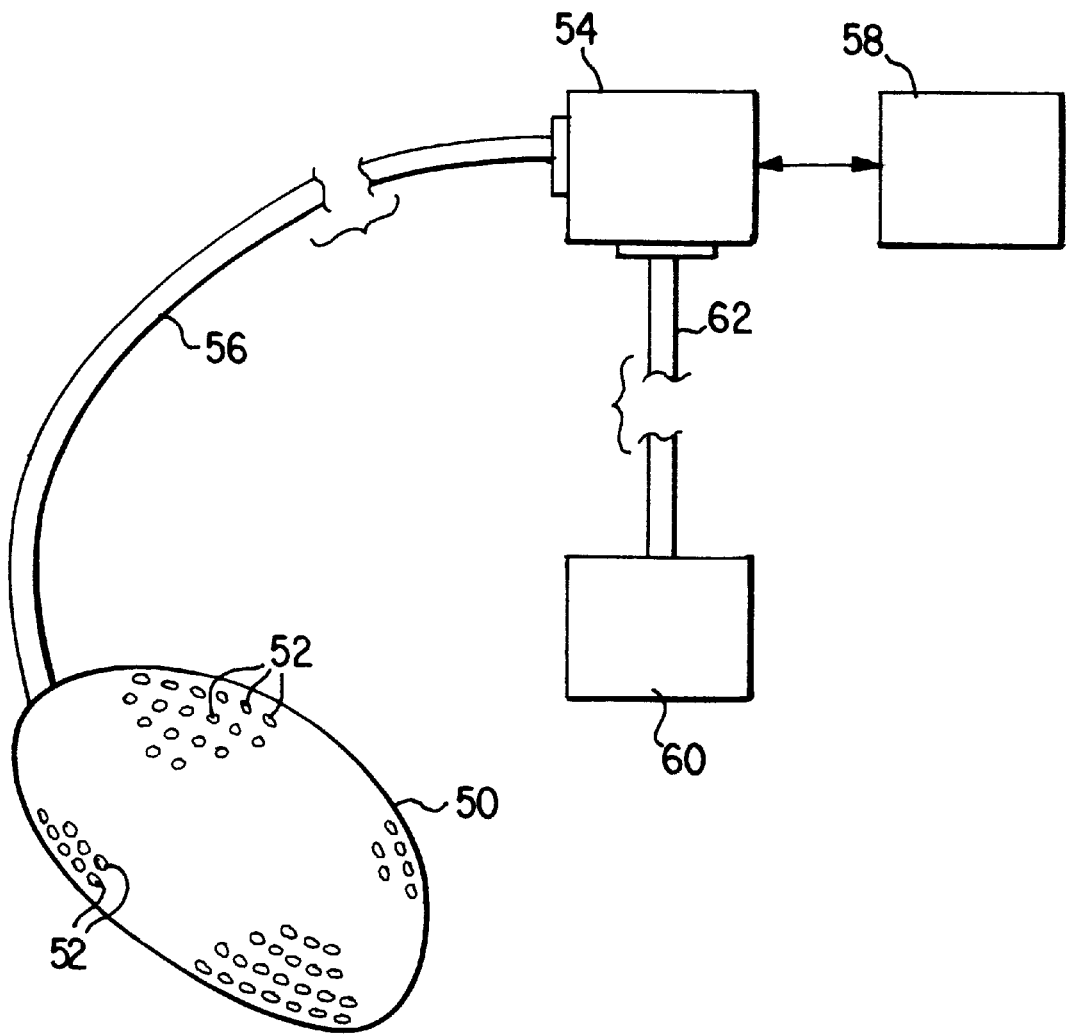
FIG. 2 shows an electrode array configuration.

FIG. 2 illustrates an alternative embodiment of a system useful for performing the methods of the present invention. The system of FIG. 2 comprises an electrode array 50 in the form of a patch which is conformable and attachable to the nipple surface. Typically, the electrode array 50 will have an area sufficient to attach to the entire nipple surface of the breast. The array will include a plurality of individual electrodes or electrode nodes disposed over one side thereof. Electrode nodes are electrically isolated and connected to a switching or multiplexing unit 54 via a cable 56. The multiplexing unit, in turn, is connected to an analyzer 58, typically a personal computer or other digital analyzer. A counterelectrode 60 is also provided and connectable to the switching unit 54 via a cable 62.

In use, the electrode array 50 of FIG. 2 would be secured to the nipple surface, optionally employing an electrically conductive gel between the electrode nodes 52 and the nipple surface. The array 50 will usually be held tightly in place over the nipple, optionally using tape or other securing fasteners. Once in place, electrical energy may be transmitted to the electrode nodes 52 from the switching unit 54 via the cable 56. Usually, the signals will be transmitted sequentially between the individual electrode nodes 52 using switching circuitry within the multiplexing unit 54. Usually, only a single electrode node 52 will be energized at a time, with the corresponding electrical characteristic being measured prior to energizing the subsequent node. Alternatively, it may be possible to energize multiple electrode nodes 52 simultaneously, particularly if the energized nodes are remote from each other to avoid interference in reading the characteristic electrical signal. Energization of the nodes and collection and analysis of the data will usually be performed by the analyzer 58, as described in more detail elsewhere herein.

The electrode array 50 may have a wide variety of specific configurations. For example, the array could comprise a plastic or other flexible, electrically non-conductive substrate having the array of electrode nodes deposited thereon by conventional thin-film techniques such as plating, CVD, photolithography, or the like. Alternatively, the membrane could be composed of a network of electrically conductive members with suitable isolation being provided to define the individual electrode nodes 52 on the surface of the array 50.

Figure 3:
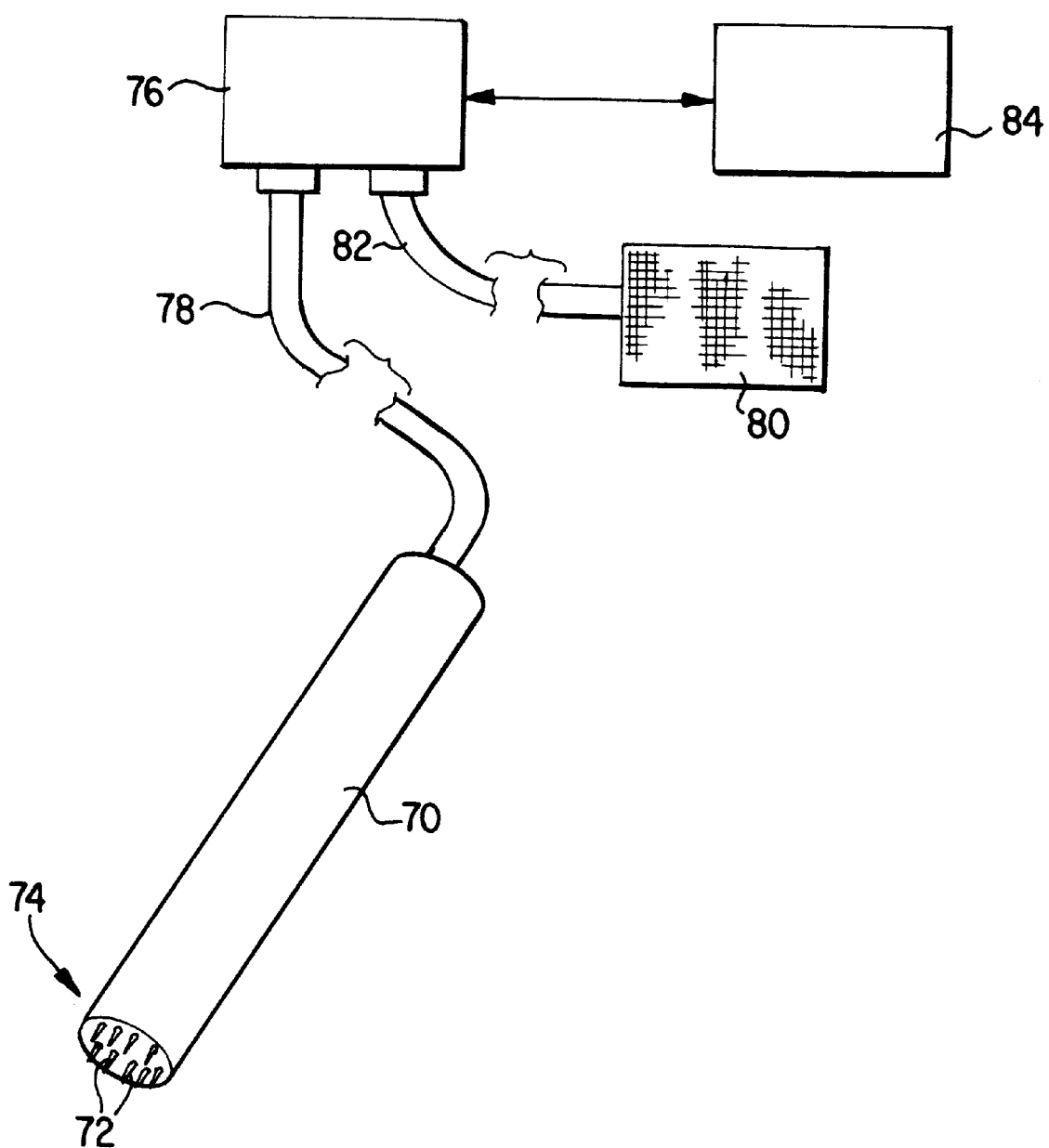
FIG. 3 shows a bundle electrode configuration comprising multiple electrodes for testing the nipple surface in a bundle formation.

A third alternative test electrode configuration is illustrated in FIG. 3. There, a probe 70 has an array electrode tips 72 formed at its distal end 74. The electrode tips 72 are isolated from each other, and individual conductors (not shown) are connected to a switching or multiplexing unit 76 via a cable 78. A counterelectrode 80 is also connectable to the multiplexing unit 76 via a cable 82. The multiplexing unit 76 may be connected to an analyzer 84, generally as described above for the system of FIG. 2. The probe 70 would be used to contact the electrode tips 72 against the nipple surface by successively probing the nipple surface at different points. The data could be collected, analyzed, and presented in any of the ways described above. The use of multiple electrode tips 72 would reduce the time required to scan or map the entire nipple surface.

The test electrode can be a single electrode moved to different locations on the surface of the nipple for each measurement taken. Measurements of characteristic electrical signal can be taken sequentially from each test electrode on the nipple surface relative to a reference electrode at the reference point on the body of the mammal for either multiple or single test electrode systems. The reference electrode may be on the nipple surface also, or may also be at the base of the breast or at the base of the nipple or at any other suitable reference point on the mammal being studied. With embodiments having multiple test electrodes, the potential and/or current to the test electrodes, and the subsequent measurements of characteristic electrical signal are coordinated with a switcher, e.g., a mechanism that switches the potential to each electrode in the bundle or array successively, and then measures the characteristic electrical signal value at each electrode in the bundle or array in succession as well.

The reference and test electrodes can be made of e.g., silver, silver/silver chloride, platinum, titanium, or other conductive material suitable for use as an electrode contacting a skin surface. Electrodes can be made as described in U.S. Pat. No. 5,217,014, U.S. Pat. No. 5,660,177, and WO 96/12439 and U.S. Pat. No. 5,810,742 with further modifications as described herein, including modifications to suit the particular purpose of the invention, namely to identify ductal orifices locations on a nipple surface. The test electrodes and the reference electrode can have lead (insulated conductive wire) to a machine capable of generating an electrical potential or current in an electrical circuit for generating the potential and measuring the characteristic electrical signal values. The machine capable of generating an electrical potential or current in an electrical circuit has the ability to generate potentials at various frequencies for making these measurements. One type of machine for generating the potential and measuring the characteristic electrical signal values can be an LCR machine (LCR stands for admittance, capacitance and resistance). The electrode wire size can be e.g., in the range of 1 $\mu$m to 1 mm diameter, e.g., a range of about 50 $\mu$m to 500 $\mu$m in diameter.

Where the test electrode is a bundle or array of multiple electrodes able to take sequential readings from different points on the nipple surface relative to a reference electrode with which a potential is generated, the multiple electrodes can be affixed to a solid support, for example polyvinyl chloride (PVC) or other polymer or plastic. The solid support can be a flexible support. Thus, the solid support may also be made of a less rigid material; e.g., mylar or other flexible solid support capable of yielding to the contour of the surface of the nipple upon pressure from the surface on the electrodes that contact the contoured surface. The solid support can be a plate, or a molded or moldable solid support, provided that the solid support is capable of yielding at least somewhat to the contours and roundness of the human nipple, or can allow the electrodes affixed to it to yield to the contours of the nipple surface. In general, an array of electrodes are electrodes fixed in a solid support at a fixed distance from each other, and a bundle of electrodes are longer electrodes bundled together in a bundle-like configuration having random spacing between the electrodes in the bundle. Either an array or a bundle can be from very few to several tens of thousands of electrodes, and either a bundle or an array can cover from a small portion of the nipple surface to the entire nipple surface.

A multi-array test electrode comprised of multiple electrodes (e.g., a range of from 10 to 100,000, e.g., particularly 100 to 10,000 electrodes) is designed to measure characteristic electrical signals over the whole nipple, and to allow the electrodes to touch the nipple surface in all places including the crevices of the nipple surface. The test electrode multi-array can have a wire to a machine capable of generating an electrical potential or current in an electrical circuit for generating the potential and measuring the characteristic electrical signal. The electrode wire size for an array of electrodes can be e.g., in the range of 1 $\mu$m to 1 mm diameter, e.g., about 50 $\mu$m to 250 $\mu$m in diameter. The electrode spacing can be about a range of 10 to 200 $\mu$m apart, e.g., about 100 $\mu$m apart. In an array having a solid support base to which all the electrodes are attached, individual electrodes can protrude below the surface of a solid support in the range from about 10 $\mu$m to 1 cm, e.g., a range from about 500 $\mu$m to about 3000 $\mu$m. The total size of the multi-array on the solid support can be about the size of the nipple. The array can also cover less than the entire surface of the nipple. The electrodes can each be connected to a lead that connects to a machine capable of generating an electrical potential or current in an electrical circuit. The lead can also be connected to a switcher that is connected to a machine capable of generating an electrical potential or current in an electrical circuit.

In addition to an array in a fixed solid support, the electrodes can be configured in a bundle by being wrapped or somehow tied or pulled together. The bundle can cover a part of or all of the nipple surface. The electrode wire size for a bundle of electrodes can be e.g., in the range of 1 $\mu$m to 1 mm diameter, e.g., about 50 $\mu$m to 250 $\mu$m in diameter. The bundle of electrodes can cover less than the whole surface of the nipple, e.g., to probe the nipple surface in quadrants using e.g., the 10 electrode probes at a time, or can cover the whole surface of the nipple. Where the goal of the bundle is to cover the entire area of the nipple surface, various sizes of bundles can be made to accommodate various nipple sizes. The electrodes can each be connected to a lead that connects to a machine capable of generating an electrical potential or current in an electrical circuit. The lead can also be connected to a switcher that is connected to a machine capable of generating an electrical potential or current in an electrical circuit.

Measuring characteristic electrical signal can comprise making measurements at a specific frequency or at a range of frequencies, using e.g., a machine capable of generating an electrical potential or current in an electrical circuit. The measurements can be made at a range of frequencies and the range can be predetermined. For example, a frequency can be in the range of 100 Hz to 1000 kHz. For a predetermined range, several frequencies can be selected, e.g., 1000 Hz, 10 kHz, 100 kHz, and 1000 kHz and tested in different locations on the surface of the nipple.

Thus, e.g., location A is probed at 3 to 10 frequencies, and location B is probed at the same 3 to 10 frequencies, and the characteristic electrical signal values at each location for each frequency can be compared. The range of frequencies used can be a random range or a predetermined range of frequencies. With regard to an embodiment having multiple test electrodes, the machine capable of generating an electrical potential or current in an electrical circuit can be connected to a switcher for relaying the potential and taking measurements at each electrode. The switcher can be connected to a machine for analyzing the electrical signals, e.g., a central processing unit (CPU) for analyzing (and capturing and storing) the data retrieved from the characteristic electrical signal measurements.

Additional features of the test electrodes can include that they are designed in an array of electrodes affixed to a solid support. The array comprises multiple electrodes so that more electrodes more efficiently contact the skin surface of the nipple. This improvement is made in order to overcome a difficulty inherent in the taking of such measurements in that the nipple surface is uneven and thus difficult to contact uniformly with an array of electrical probes. Probes of fixed length attached to a solid support may be unable to contact the nipple surface with fidelity. Modification includes a probe array affixed to a solid support so that the electrodes can move up and down relative to the solid support and the nipple surface. Thus, where a particular electrode is over a "valley" on the nipple surface, the electrode may be pushed down farther (relative to its neighbor electrodes) and make contact with the nipple surface in the valley. Conversely, where an electrode is over a "hill" on the nipple surface, that electrode may be pushed up relative to its neighbor electrodes and thus make contact with the nipple surface on the hill. In short, the electrodes can be movable in their bundle or array to accommodate the contours of the nipple surface.

The electrodes in an array or a bundle can move up and down in a variety of ways. First, if the electrodes are attached to a solid support, they are still able to move up and down relative to that solid support. An "O" ring can be provided that puts weight on the electrode close to the nipple surface, encouraging the electrode to contact the surface completely. The "O" rings can be coated with a non-conductive material. "O" rings also can enable a piston-like action for the electrode, allowing a range of up and down movement so that the electrode can be pushed against the nipple surface. For example, where a piston mechanism can be provided for each electrode such that the electrode can slide up and down in a piston sleeve, to make contact with the nipple surface. The electrodes may also be fashioned like pins in a board, such that upon contact with a skin surface the electrode retreats only to the extent that the nipple surface encourages retreat (as in a hill), and they remain lowered where a valley is present on the nipple surface. Springs can be placed between the solid support and the electrodes to provide a mechanism to push the electrode tips closer to the nipple surface, e.g., especially where a valley is present.

The bundle of electrodes may also comprise separate electrodes encased in a glass capillary tubes which provide a cylinder for facilitating the up and down movement of the electrodes in order to contact the uneven nipple surface. The capillary tubes can be closed with a film through which a potential is still permitted to travel on each end so that the electrodes cannot fall out of the capillary tubes. The distal end of the electrode can be connected to a lead which is connected to a switcher and then a machine capable of generating an electrical potential or current in an electrical circuit.

Additionally, where the test electrode or the array or bundle of test electrodes is placed over the nipple surface under a vacuum, e.g., as an additional part of a vacuum suction apparatus, the nipple surface is made to be more flat (by the vacuum that pulls on the nipple surface) and better contact with the skin surface by probe electrodes is therefore facilitated. A breast pump can provide vacuum to the surface of the nipple, and the pump may have thin threads or wires to allow positioning of a bundle or array of electrodes directly on the surface of the nipple. The reference electrode can be placed at the base of the breast, or some other suitable location. Adjustments to the position of the test electrodes can be made prior to application of a vacuum. A vacuum can provide an environment that causes the nipple surface to become smoother or to have fewer contours. The solid support of an array can be made of mylar so that the electrodes in the array can conform to the nipple surface better than they would if affixed to a rigid solid support. Additionally, the electrodes can be moveable as described earlier. Characteristic electrical signal measurements can be taken from the nipple surface under the vacuum pressure.

Where a single test electrode is used under vacuum pressure, the reference electrode can be placed on the nipple surface or at another suitable location, and the characteristic electrical signal measurements taken while the nipple surface is under vacuum pressure.

After placement of the reference electrode and the test electrode on their respective parts of the mammal to be analyzed, (e.g., the reference electrode is placed at the base of the breast, and the test electrode is placed at the nipple surface) a reference potential can be established between the two electrodes. Although the invention is not limited to theories of how the system works, it is proposed that a potential between a reference electrode and a test electrode will preferentially travel through the breast ducts with a lower characteristic electrical signal value. The electrodes can be connected to leads that connect to a machine, for example a machine capable of generating an electrical potential or current in an electrical circuit, capable of establishing a potential between the electrodes and of measuring characteristic electrical signal within the circuit.

The machine can be one essentially as described in U.S. Pat. No. 5,143,079, WO 96/12439, U.S. Pat. No. 5,810,742, U.S. Pat. No. 5,678,547, U.S. Pat. No. 4,458,694 or U.S. Pat. No. 4,291,708. The machine can be capable of generating an electrical potential, and can also include a machine for analyzing the electrical signal, (e.g., a central processing unit (CPU)) for making analysis of the measurements that are taken from the potential generated between two electrodes. Characteristic electrical signal is a value that can be measured by virtue of the potential difference between the two electrodes. Other parameters that can be derived from an characteristic electrical signal measurement including resistance or capacitance can also be measured and used to compare the probe locations. Thus, for example, point A on the nipple surface may have a lower characteristic electrical signal measurement than point B on the nipple surface, indicating the likelihood that point A is a ductal orifice. It is also important to note that a ductal orifice may be indicated by higher characteristic electrical signal where the ductal orifice has a keratin plug, as keratin plugs will generally provide for higher characteristic electrical signal of the potential. The invention accordingly also provides that the nipple can be dekeratinized with an appropriately effective dekeratinizing agent before the electrical measurements are taken. Dekeratinizing agents include those known in the art, e.g., acetic acid at a dekeratinizing strength, empigen, cerumenex, and preparative agents containing alcohol.

To identify a ductal orifice, a test electrode may be moved across the nipple surface, testing for areas of characteristic electrical signal variation, including areas of low characteristic electrical signal and high characteristic electrical signal. At a particular area of low characteristic electrical signal, for example, (if low signal indicates a ductal orifice) a guidewire can be inserted within a ductal orifice, and the procedure continued until all ducts have been located. The placement of the guidewire provides the practitioner with the opportunity to access the duct later, after the scanning of the nipple surface is complete and all the ducts have been identified. The guidewires placed in the ducts also provide an opportunity to take a photograph of the nipple with guidewires extending from it for recording the locations of the ductal orifices.

The nipple can be coated with a conductive gel sensitive to impedance (e.g., a liquid crystal film). Additionally, a matrix or screen about the area of a nipple surface having multiple tiny holes from a cross-hatch of a non-conductive wire or mesh (e.g., nylon wire) grid can be placed over the nipple. A reference electrode can be placed at the base of the breast or any other appropriate location, and a test electrode at the nipple, e.g., at the side of the nipple so as not to interfere with the matrix and gel on the top of the nipple surface. After a potential or voltage and/or current is applied to the system, a machine electronically registers characteristic electrical signal values from the conductive gel to show e.g., a map of spikes where low characteristic electrical signal values exist, indicating likely candidate locations of ductal orifices on the surface of the nipple. Through the matrix or screen at the points of low or high characteristic electrical signal, guidewires can be threaded into the ductal orifices (depending on which signals are indicative of a ductal orifice with the given signal). The matrix or screen can thus provide information about the nipple surface that registers an characteristic electrical signal variation, and a corresponding local for each ductal orifice on the surface.

The test electrode may also be equipped with a pen or other marking device, so that upon identification of a ductal orifice, the orifice can be marked with the pen, or other device, for photograph or for later access. The marking can comprise e.g., fluorescent marking technology. The marking can be temporary (e.g., removable), semi-permanent, or permanent, e.g., as with a kind of tattoo on the nipple surface that is removable, semi-permanent or permanent. The tattoo can comprise injection of a biocompatible dye into the surface of the nipple. In any event, the markings can be photographed for the patient's records. The markings can be invisible to the naked eye, but their visualization can be activated with a special light or other visualization aid.

Where the test electrode is an array of electrodes, a marking system can be incorporated into the array, including the ability to mark the electrode registering a low characteristic electrical signal measurement indicative of a ductal orifice, and the marked electrode then marks the skin at that spot, e.g., with a topical dye or pen marking system.

The ductal orifices can be imaged as described by a photograph of a visual marker such as an inserted guidewire, a tattoo or other mark at the orifice on the surface of the nipple. A current sensitive film (e.g., a liquid crystal film) can be placed on the nipple to show a map of the characteristic electrical signals on the nipple surface indicating areas of likely location of ductal orifices. The electronic values can be printed from the computer. Evidence of any characteristic electrical signals from the nipples surface can be imaged electronically, by photo, and recordation of numerical values corresponding to the signals.

The machine connected to the leads may also contain a machine for analyzing the electrical signal, (e.g., a central processing unit (CPU)) for processing the electrical signals generated by the measured values of characteristic electrical signals received from the test probe at the nipple surface. The machine for analyzing the electrical signal can generate electronic signals that provide an image or map of the nipple surface. Electronic imaging can provide a practitioner with a real time image to use in accessing the ducts. An electronic image can also provide the opportunity for generating a printed image of the nipple surface that indicates the location of the ductal orifices for the patient's records. The machine for analyzing the electrical signal can also capture the characteristic electrical signal values and store them for later access. The practitioner can work in real time from the electronic image, or can use the printed image to provide a map to the ductal orifices.

The ducts can be accessed for any purpose, including providing a medical treatment or procedure comprising therapeutic, prophylactic, diagnostic or prognostic purposes. For example, tissue or fluid can be removed from the duct, or agents can be delivered to a duct or ducts. The test electrode can be operated while access of the ductal orifice is desired. Thus, upon identification of a ductal orifice, access can be made with a guidewire as describe herein, or other accessing device. The access can be accomplished by, e.g., a catheter, cannula, guidewire or other medical probe suitable for ductal access. Purposes of access can include, e.g., removing fluid or administering an agent or marking the ducts as with guidewires, or other analysis or manipulation of the duct. The probe can also be an imaging probe where desired, for example a ductscope or other imaging device capable of penetrating a breast duct once accessed.

Characteristic electrical signal measuring devices can be made essentially as described in WO 96/12439 to TransScan, U.S. Pat. No. 5,810,742 also to TransScan, U.S. Pat. No. 5,143,079 to Yeda Research and Development Co., U.S. Pat. No. 5,678,547 to Biofield Corp., and U.S. Pat. No. 5,660,177 to Biofield Corp. Modifications can be made to the devices described in these patents and publications and herein, including adaptations made in order to read electrical potentials at the surface of a nipple, particularly those at ductal orifices. Thus, electrodes are placed at some point on the body, e.g., at the base of the breast, and on the nipple surface in order that characteristic electrical signal between these two points is measurable after a potential is applied between the electrodes completing a circuit. The devices include a reference electrode for placement at a point on the body other than the location of the test electrode, a test electrode for placement on the surface of the nipple, leads from each electrode to a machine capable of generating an electrical potential between the two electrodes and of measuring a value of a characteristic electrical signal existing at a given test spot, e.g., a machine capable of generating an electrical potential or current in an electrical circuit.

Such a device used in the method of identifying ductal orifices is used to take multiple comparable measurements of characteristic electrical signal at various points on the nipple surface. The ductal orifices are identified, e.g., by a characteristic electrical signal. Thus where a characteristic electrical signal is detected, a ductal orifice on the nipple surface can be identified. The detection is made based on characteristic electrical signal measurements at that spot as compared preferably to a reference value (e.g., a value established based on a survey of likely values for ductal orifices on nipple surfaces), also with reference to a potential and/or current created in a closed circuit with the reference electrode. Ultimately, whether a particular spot on the nipple surface is or is not a ductal orifice can be determined by whether it can be cannulated or accessed with a guidewire after identification.

The devices for use in the invention can also comprises an ability to image characteristic electrical signal electronically, or the device can provide for a photograph to be taken of a marked nipple surface. An electronic image, a printed image, and an image as a result of exposure to sensitive film, including e.g., X-ray film can be generated from the device or upon generation of a potential and/or current through the breast by the device.

The electrodes useful for practicing the method using characteristic electrical signal can be made essentially as described in U.S. Pat. No. 5,217,014 to Biofield Corp., and WO 96/12439 with modifications appropriate to the diminutive size of the nipple surface and the ductal orifices relative to the items being detected in these patents and publications, and also with regard to the reduced conductance per ductal orifice that it is the object to identify. The test electrodes can be designed as described herein, e.g., a single test electrode moved sequentially to locations on the nipple surface and multi-array test electrodes attached to a solid support and contacting the nipple surface. Readings from the multi-array test electrodes are still taken sequentially at each electrode with reference to a reference electrode which can also be located at the nipple surface, or at another location on the mammal.

The invention also provides a kit for identifying a breast nipple ductal orifice comprising a reference electrode and a test electrode capable of being connected to a machine capable of generating an electrical potential or current in an electrical circuit. The machine capable of generating an electrical potential or current in an electrical circuit can generate a potential between the two electrodes and measure a characteristic electrical signal value at a given location on a nipple surface. The kit can further include an accessing element for accessing the ductal orifice once identified. The accessing element can comprise, e.g., a guidewire, a cannula or a catheter. The machine capable of generating an electrical potential or current in an electrical circuit can be operably connected to a machine for analyzing the electrical signal, (e.g., a central processing unit (CPU)) e.g., comprising a computer program capable of analyzing a plurality of characteristic electrical signal measurements taken from the nipple surface. The machine for analyzing the electrical signal can also be capable of capturing the characteristic electrical signal values as electronic information, storing this information, and imaging it, e.g., either on the computer screen, on a printed piece of paper, in a graph, or other useful image. The kit can further comprises instructions for use of the kit. The kit can further comprise an element to mark the duct location on the nipple surface once the orifice is identified, e.g., a pen capable of leaving an ink marking on the nipple surface or a tool capable of generating a tattoo marking on the nipple surface, or a guidewire that can be placed within the duct to mark the ductal orifice location. A mark generated can be visible to the naked eye or invisible except with the use of a special, e.g., fluorescent, light or other aid. The kit can further comprise a non-conductive wire mesh screen for placement over the nipple surface, and a conductive gel for spreading on the nipple surface for generating an characteristic electrical signal map of the nipple surface.

Figure 4:
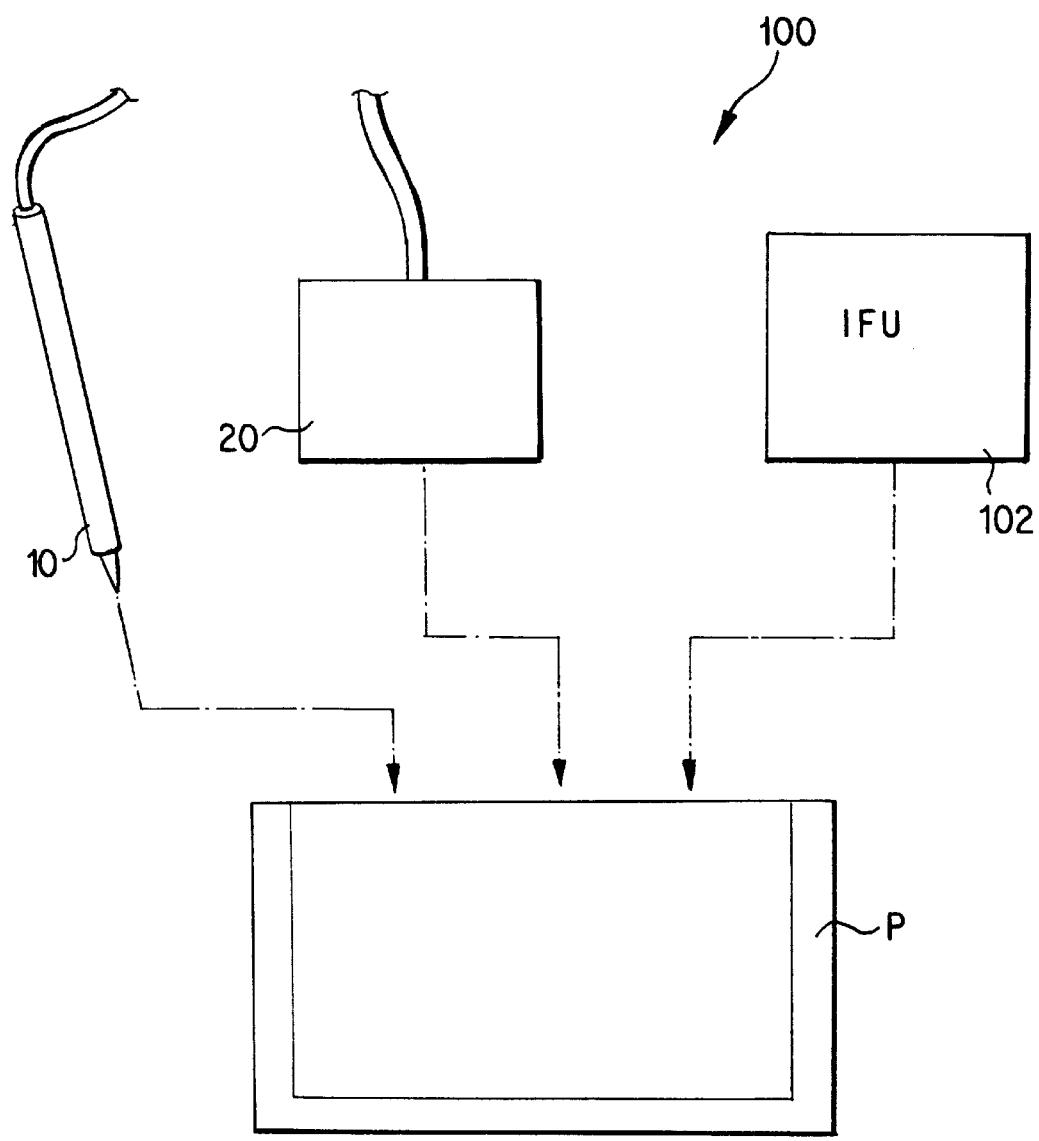
FIG. 4 illustrates a first embodiment of a kit constructed in accordance with the principles of the present invention.
Figure 5:
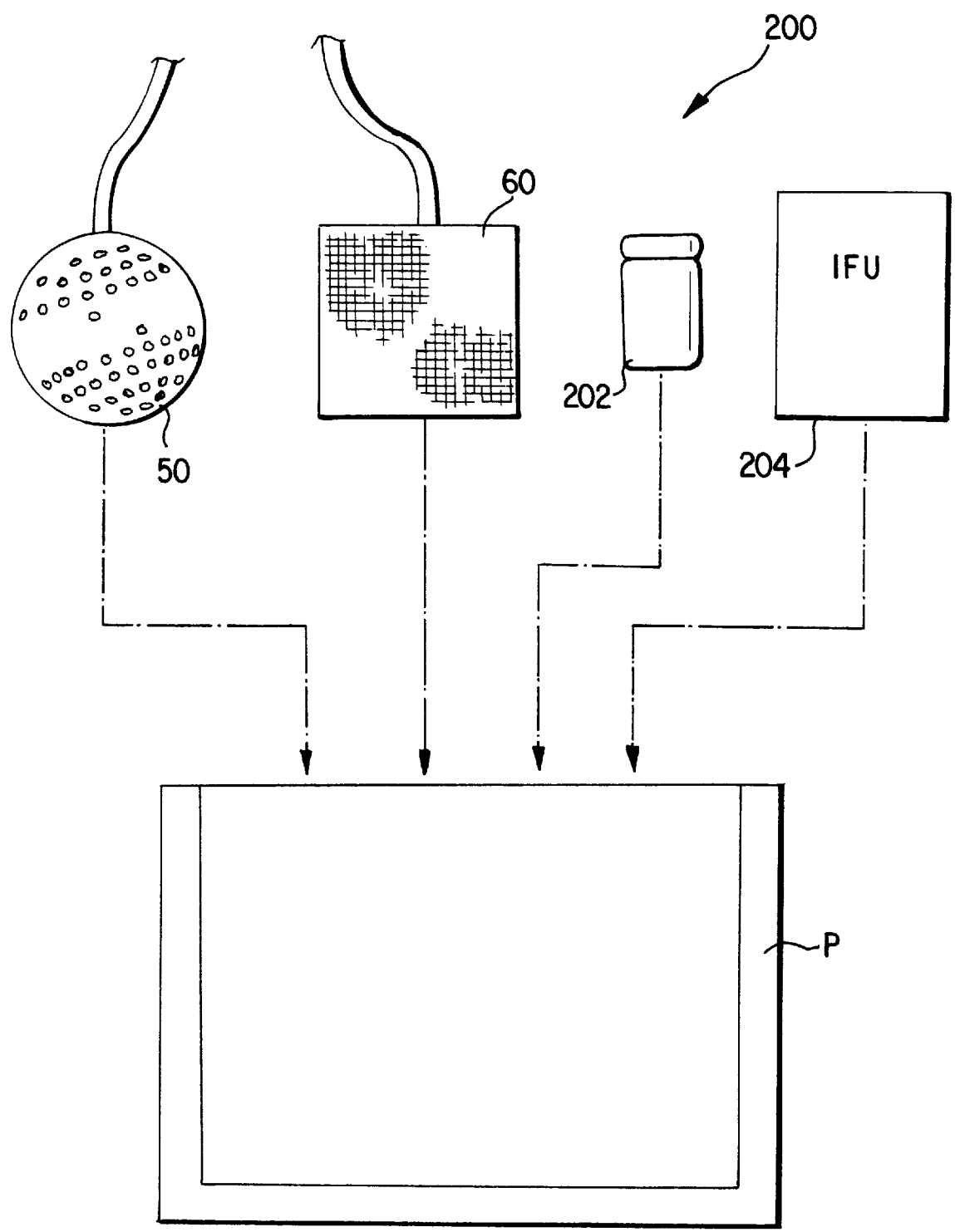
FIG. 5 illustrates a second embodiment of a kit constructed in accordance with the principles of the present invention.

Kits constructed in accordance with the principles of the present invention are illustrated in FIGS. 4 and 5. The kit 100 of FIG. 4 comprises a probe 10 and counterelectrode 20 as described previously with reference to FIG. 1. In addition to these kit components, the kit 100 will usually include instructions for use 102 setting forth any of the methods described herein, as well as packaging in the form of a pouch P or other conventional medical device package, such as a tube, bag, tray, box, or the like. Usually, at least the probe 10 and counterelectrode 20 will be maintained sterilely within the packaging, and the instructions for use 102 may be provided on a separate package insert (as illustrated) or may printed in whole or in part on the packaging.

Kit 200 is illustrated in FIG. 5 and includes an electrode array 50 and counterelectrode 60 as described previously in connection with FIG. 5. In addition to these kit components, the kit 200 may further comprise an electrically conductive gel 202, instructions for use 204, and packaging P. The electrically conductive gel is optionally used in the methods where it is applied to the nipple before the electrode array 50 is secured thereto. Instructions for use 204 may set forth any of the methods described herein which utilize an electrode array. The packaging may be pouch P or any conventional form of medical device packaging as described above.

The following is a table to illustrate applications of the method of the invention to identification of ductal orifices of several patients. The N=? column refers to the number of contact points of electrode on a nipple surface.

TABLE I

| human/nipple (right or left) | N = ? | potential | impedance range | capacitance range | e.g.: ducts located | guidewire photo? |
|---|---|---|---|---|---|---|
| A right | 1000 | 2 kiloHz | 2 kiloOhms to 18 megaOhms | not taken | 10 | no |
| A left | 1000 | 2 kiloHz | 2 kiloOhms to 18 megaOhms | not taken | 8 | no |
| B right | 100 | 5 kiloHz | not taken | 1 nanoFarad to 500 picoFarad | 6 | yes |
| B left | 100 | 5 kiloHz | not taken | 1 nanoFarad to 500 picoFarad | 7 | yes |
| C right | 200 | 3 kiloHz | 2 kiloOhms to 30 megaOhms | not taken | 12 | yes |
| C left | 200 | 3 kiloHz | 2 kiloOhms to 30 megaOhms | not taken | 9 | yes |
| D right | 10,000 | 7 kiloHz | 2 kiloOhms to 10 megaOhms | 1 nanoFarad to 500 picoFarad | 7 | yes |
| D left | 10,000 | 7 kiloHz | 2 kiloOhms to 10 megaOhms | 1 nanoFarad to 500 picoFarad | 9 | yes |
| E right | 10 | 10 kiloHz | 10 kiloOhms to 200 kiloOhms | not taken | 4 | yes |
| E left | 10 | 10 kiloHz | 10 kiloOhms to 200 kiloOhms | not taken | 6 | yes |

EXAMPLES

1. Electrical Impedance for Identifying a Ductal Orifice

A human patient is connected with a multi-array test electrode having many electrical probes movably affixed to a mylar sheet that approximately covers the surface of the nipple. Each electrode is 100 μm thick and the electrodes are 100 μm apart. The electrodes extend from the mylar by 200 μm. The electrodes have the ability to rest on the surface of the nipple, and thus to slide up or down depending on a high or low point in the contour of the nipple surface. A reference probe (electrode) is placed at the base of the breast and the two probes (electrodes) are attached to leads to an LCR machine capable of generating a potential between the test electrodes and the reference electrode, and capable of measuring characteristic electrical signal. An electronic image of the characteristic electrical signal values is made based on the location of the electrodes in the array, and can be captured, analyzed and stored in a machine for analyzing the electrical signal (e.g., a central processing unit (CPU)), e.g., comprising a computer program for analyzing multiple characteristic electrical signal values. The electronic information captured by the machine for analyzing the electrical signal also generates an electronic "picture" on a computer screen of the nipple surface that identifies in particular regions of high and low characteristic electrical signal. Where the characteristic electrical signal is an impedance value, regions of low impedance value are regions that become candidate locations of ductal orifices. High impedance values are candidate regions for locations of ductal orifices having keratin plugs. The electronic image can be printed for placing in the patient's medical records. The entire process is repeated on the left nipple.

2. Electrical Map of the Nipple Surface

A human nipple is dekeratinized and coated with a liquid crystal gel capable of registering a characteristic electrical signal, and a screen (a nylon wire matrix having tiny squares formed of the wire cross-hatch grid). The screen having a nylon wire grid is the size of the area of the nipple and is placed on the nipple. A reference electrode is placed at the base of the breast, and a test electrode is placed on the surface of the nipple. A potential and/or current is generated through the breast, and an electrical map is created by the variation of characteristic electrical signal values on the surface of the nipple. The readings of characteristic electrical signal measured in Ohms by the machine capable of generating an electrical potential or current in an electrical circuit connected to the reference and test electrodes indicate likely locations of a ductal orifice with reference to a reference value (e.g., a value below which or above which a ductal orifice is indicated). An electronic picture of the nipple surface is retrieved from a machine for analyzing the electrical signal connected to the machine capable of generating an electrical potential or current in an electrical circuit. The machine for analyzing the electrical signal captures the electronic data comprising characteristic electrical signal values and analyzes it in a computer program, which data can be saved to a hard drive for later use. Guidewires are placed in the regions of characteristic electrical signal indicating a ductal orifice through the fine holes of the screen. Once the entire nipple has a guidewire placed in all regions of characteristic electrical signal, i.e., the ductal orifices, the screen is removed. The guidewire-marked nipple is photographed for the patient's records. The entire process is repeated for the left nipple.

3. Characteristic Electrical Signal Measurements in Rabbit and Human Breasts

Electrical measurements of impedance and/or capacitance were made using platinum or silver-silver chloride electrodes having a tip of between 1 μm and 1 mm. The electrode was manually placed at different locations on the surface of a nipple on a dead rabbit pelt (n=100 locations), the surface of a live rabbit nipple (n=90 locations), a masticated detached human breast (n=130 locations), and a human breast (n=70 locations). Measurements made on the surface of the human nipple at frequencies between 10 Hz and 100 kiloHz showed differences between the milk duct and the surrounding non-duct area of the nipple by detection of impedance measurements (as a characteristic electrical signal) of between 2 kiloOhms and 18 megaOhms and higher with some characteristic electrical signals too high to register. Differences in capacitance varied between the milk duct and the surrounding non-duct area of the nipple with values ranging from 1 nanoFarad to 500 picoFarad. Low impedance indicated a location of a ductal orifice that was verified by accessing an orifice at that location with a guidewire. Locations that could be accessed by a guidewire were registered as positive identification of a ductal orifice.

4. Characteristic Electrical Signal Measurements Using a Bundle of 6 Electrodes on Masticated Nipple Surface A bundle of electrodes was constructed having 6 electrodes in the bundle. Galactography needles (available from Manan, Inc. located at Gainsburg, Fla.) were cut to 3.5 cm. Cut needles were each inserted into glass capillary tubes (one needle per tube) such that 1 mm of needle protruded out of the bottom of the tube. Six capillary tubes having needles were bundled together. Each needle was connected to a lead wire at the top of the capillary tube, and the lead was connected to an LCR meter. A reference electrode was placed on the areola of a masticated breast. A potential was generated in each of the 6 electrodes (needles) at 36 different spots on the masticated breast nipple surface, i.e., the bundle was moved to 6 different locations or spots on the nipple surface. Potentials were generated at 1 kilohertz and 10 kilohertz at each of the 6 spots where the bundle rested. Impedance measurements taken at 1 kilohertz ranged from 20 kiloOhms to 1 megaOhm; impedance measurements taken at 10 kiloHz ranged from 10 kiloOhms to 144 kiloOhms as show below in the Table II below.

TABLE II

Results of Bundle Electrode Test of Mastected Breast Nipple Surface
-----------Frequency---------

| spot/electrode | 1 kiloHz | 10 kiloHz | conclusions |
| --- | --- | --- | --- |
| spot 1/electrode 1 | 71 kiloOhms | 71 kiloOhms | |
| 1/2 | 142 | 144 | based on both measurements (1 and 10 kiloHz) high impedance; possible duct |
| 1/3 | 29 | 27 | |
| 1/4 | 29 | 26 | |
| 1/5 | 20 | 19 | |
| 1/6 | 29 | 28 | |
| spot 2/electrode 1 | 28 | 13 | |
| 2/2 | 29 | 18 | |
| 2/3 | 100 | 22 | based on measurement at 1 kiloHz, high impedance; possible duct |
| 2/4 | 30 | 13 | |
| 2/5 | 25 | 11 | based on measurement at 10 kiloHz, low impedance; possible duct |
| 2/6 | 23 | 14 | |
| spot 3/electrode 1 | 29 | 20 | |
| 3/2 | 243 | 56 | based on measurement at 1 kiloHz, high impedance; possible duct |
| 3/3 | 208 | 52 | based on measurement at 1 kiloHz, high impedance; possible duct |
| 3/4 | 186 | 52 | |
| 3/5 | 124 | 30 | |
| 3/6 | 61 | 22 | |
| spot 4/electrode 1 | 22 | 17 | |

TABLE II-continued

Results of Bundle Electrode Test of Mastected Breast Nipple Surface

| spot/electrode | Frequency | | conclusions |
|---|---|---|---|
| | 1 kiloHz | 10 kiloHz | |
| 4/2 | 153 | 150 | based on both measurements (1 and 10 kiloHz) high impedance; possible duct |
| 4/3 | 46 | 13 | |
| 4/4 | 63 | 18 | |
| 4/5 | 80 | 27 | |
| 4/6 | 40 | 18 | |
| spot 5/electrode 1 | 85 | not taken | |
| 5/2 | 69 | not taken | |
| 5/3 | 11 | not taken | |
| 5/4 | 215 | not taken | |
| 5/5 | 308 | not taken | |
| 5/6 | 1000 | not taken | based on measurement taken at 1 kiloHz; high impedance; possible duct |
| spot 6/electrode 1 | 128 | 32 | |
| 6/2 | 82 | 29 | |
| 6/3 | 520 | 69 | based on measurement taken at 1 kiloHz; high impedance; possible duct |
| 6/4 | 215 | 26 | |
| 6/5 | 33 | 19 | |
| 6/6 | 32 | 15 | |

List of References

1. Wrensch M R, Petrakis N L, King E B, Milke R, Mason L, Chew K L, Lee M M, Ernster V L, Hilton J F, Schweitzer R, Goodson W H, and Hunt T K, (1991) *Am. J. Epidemiology*, v. 135 (2): 130–141.
2. King, E B, Chew K L, Petrakis N L, Ernster V L, (1983) *JNCI* 71 (6) 1115–1121.
3. Papanicolaou G N, Holmquist D G, Bader G M, Falk E A (1958) *Cancer*, 11:377–409.
4. Goodson W H & King E B, THE BREAST: Comprehensive Management of enign and Malignant Diseases; *Chapter 4: Discharges and Secretions of the Nipple* volume 1; pp. 51–74 ($2^{nd}$ Ed. 1998; Eds. Kirby & Copeland, Philadelphia, Pa.)
5. Love & Barsky, (1996) Lancet 348: 997–999
6. Barsky & Love (1996) "Pathological analysis of breast duct endoscoped mastectomies" Laboratory Investigation, Modem Pathology, Abstract 67
7. Lewis (1997) Biophotonics International, pages 27–28, May/June 1997
8. Sartorious (1995) Breast Cancer Res. Treat. 35: 255–266
9. Sartorious (1987) Contrast Ductography for the recognition and localization of benign and malignant breast lesions: An improved technique" in Logan (ed.) Breast Carcinoma, New York, Wiley pp. 281–300
10. Petrakis (1993) Cancer Epidem. Biomarker Prev. 2:3–10
11. Petrakis (1986) Breast Cancer Res. Treat 8: 7–19
12. Wrensch et al (1992) Am. J. Epidem. 135:130–141
13. Wrensch et al (1990) Breast Cancer Res Treat 15: 39–21
14. Wrensch et al (1989) Cancer Res. 49:2168–2174
15. Makita et al (1991) Breast Cancer Res Treat 18: 179–188
16. Okazaki et al (1991) Jpn J. Clin. Oncol. 21:188–193
17. Diner et al (1981) American J. Radiology 137: 853
18. Tabar et al (1983) Radiology 149: 31
19. Threatt et al (1987) Ductography p. 119 Basset and Gold eds, Grune & Stratton, Orlando
20. Pansera F (1990) Medical Hypotheses 33: 107–111
21. Faupel and Hsu, (1996) *Electropotentials in the clinical assessment of breast neoplasia*, Dixon eds 37–44

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying a ductal orifice on a nipple of a mammalian breast said method comprising:
    engaging a reference electrode against a surface on the body of the mammal;
    engaging a test electrode to a test location on a nipple surface;
    applying at least one of an electrical current and a potential between the reference electrode and the test electrode;
    measuring a characteristic electrical signal produced in response to the at least one of the applied electrical current and the potential; and
    comparing the measured value to a base electrical value in order to determine a likelihood that the test location on the nipple surface comprises a ductal orifice.

2. A method as in claim 1, wherein the base electrical value is a predetermined value.

3. A method as in claim 1, wherein the reference electrode is engaged on the body of the mammal at a location selected from the group consisting of the base of the breast, the base of the nipple, the surface of the nipple, the areola of the nipple, and an abdominal or chest surface of the mammal.

4. A method as in claim 1, wherein engaging the test electrode comprises sequentially engaging the test electrode at different locations on the nipple surface so that an array of measured values is produced in order to determine a likelihood that any given location comprises a ductal orifice.

5. A method as in claim 4, wherein the base electrical value is a predetermined value.

6. A method as in claim 1, wherein the test electrode comprises multiple electrodes placed at the surface of the nipple.

7. A method as in claim 6, wherein the multiple electrodes conform to the surface of the nipple.

8. A method as in claim 1, wherein measuring a characteristic electrical signal comprises making measurements at a specific frequency or at a range of frequencies.

9. A method as in claim 1, wherein comparing the measured valve to a base electrical value further comprises capturing an image of the measured value.

10. A method as in claim 1, wherein comparing the measured valve to a base electrical value further comprises receiving a numerical value of the comparison.

11. A method as in claim 1, further comprising receiving an audible signal indicator upon likelihood that the location on the nipple surface comprises a ductal orifice.

12. A kit for identifying a ductal orifice on a breast nipple comprising:

a reference electrode capable of being engaged against a body surface;

a test electrode capable of being engaged against different locations on the breast nipple, wherein both electrodes are capable of being connected to a source that creates an electrical potential between the two electrodes; a unit for measuring a characteristic electrical signal; and a marking element capable of marking the duct location on the nipple surface once the orifice is identified.

13. A kit as in claim 12, further comprising an accessing element for accessing the ductal orifice once identified.

14. A kit as in claim 13, wherein the accessing element comprises an element capable of accessing a ductal orifice selected from the group consisting of a guidewire, a cannula, and a catheter.

15. A kit as in claim 12 wherein the marking element comprises an element selected from the group consisting of a pen capable of leaving an ink marking on the nipple surface and a tool capable of generating a tattoo marking on the nipple surface.

16. A kit as in claim 12, wherein the reference electrode and test electrodes comprise a non-conductive wire mesh screen, and wherein the kit further comprises a conductive gel for placing on the nipple surface for generating a map of the nipple surface.

17. A kit as in any of claims 12–14, 15 or 16, further comprising instructions for use.

18. A kit as in claim 12, further comprising instructions for use setting forth a method comprising:

engaging the reference electrode against a surface on a body of a mammal;

engaging the test electrode to a test location on a nipple surface;

applying at least one of an electrical current and a potential between the reference electrode and the test electrode;

measuring a characteristic electrical signal produced in response to the at least one of the applied electrical current and the potential; and comparing the measured value to a base value in order to determine a likelihood that the test location on the nipple surface comprises a ductal orifice.

19. A kit for identifying a ductal orifice on a breast nipple comprising:

a reference electrode capable of being engaged against a body surface;

a test electrode capable of being engaged against different locations on the breast nipple, wherein both electrodes are capable of being connected to a source that creates an electrical potential between the two electrodes; a unit for measuring a characteristic electrical signal; and an accessing element for accessing the ductal orifice once identified.

20. A kit as in claim 19, wherein the accessing element comprises an element capable of accessing a ductal orifice selected from the group consisting of a guidewire, a cannula, and a catheter.

21. A kit as in claim 19, further comprising a marking element capable of marking the duct location on the nipple surface once the orifice is identified.

22. A kit as in claim 21, wherein the marking element comprises an element selected from the group consisting of a pen capable of leaving an ink marking on the nipple surface and a tool capable of generating a tattoo marking on the nipple surface.

23. A kit as in claim 19, wherein the reference electrode and test electrodes comprises a non-conductive wire mesh screen, and wherein the kit further comprises a conductive gel for placing on the nipple surface for generating a map of the nipple surface.

24. A kit as in any of claims 19–23, further comprising instructions for use.

25. A kit as in claim 19, further comprising instructions for use setting forth a method comprising:

engaging the reference electrode against a surface on a body of a mammal;

engaging the test electrode to a test location on a nipple surface;

applying at least one of an electrical current and a potential between the reference electrode and the test electrode;

measuring a characteristic electrical signal produced in response to the at least one of the applied electrical current and the potential; and comparing the measured value to a base value in order to determine a likelihood that the test location on the nipple surface comprises a ductal orifice.

* * * * *